United States Patent [19]

Chapman et al.

[11] 4,112,238

[45] Sep. 5, 1978

[54] METHOD FOR THE PREPARATION OF PURE 2-ETHYLHEXYL GALLATE

[75] Inventors: Douglas W. Chapman; Hugh C. Bertsch, both of St. Louis, Mo.

[73] Assignee: Mallinckrodt, Inc., St. Louis, Mo.

[21] Appl. No.: 769,828

[22] Filed: Feb. 17, 1977

[51] Int. Cl.² .................. C07C 67/48; C07C 69/88
[52] U.S. Cl. ................................................. 560/70
[58] Field of Search ........................................ 560/70

[56] References Cited

PUBLICATIONS

Nagakura, et al., as cited in CA, 78, 159259y and 159260s.

*Primary Examiner*—Jane S. Myers
*Attorney, Agent, or Firm*—M. D. Madsen

[57] ABSTRACT

Crude 2-ethylhexyl gallate is purified by crystallizing it from a system containing an aliphatic hydrocarbon solvent such as hexane and a small proportion of 2-ethylhexanol.

12 Claims, No Drawings

METHOD FOR THE PREPARATION OF PURE 2-ETHYLHEXYL GALLATE

BACKGROUND OF THE INVENTION

This invention relates to the field of organic chemistry and more particularly to the preparation of pure 2-ethylhexyl gallate.

Various alkyl esters of gallic acid have been used as antioxidants/stabilizers in a number of food, drug and industrial chemical formulations. Such esters have also found application as components of chromogenic combinations in pressure-sensitive copying compositions. Such esters may be prepared by the reaction of gallic acid with the appropriate alcohol. Gallic acid is obtained by the hydrolytic degradation of naturally occuring gallotannins, coupled with appropriate purification procedures.

The esterification of gallic acid with an alcohol normally yields a crude ester product which contains a variety of impurities, some colored, carried over as impurites in the gallic acid and/or as a result of side reactions associated with the esterification. Most applications of such esters require that the ester be relatively free of impurities, particularly of colored bodies.

In the production of the 2-ethylhexyl ester of gallic acid, it has been common practice to crystallize the crude esterification product from a xylene solution. Such treatment produces very erratic results. On rare occasions it yields a readily filtrable product which is essentially colorless and free flowing. However, in most instances, this treatment produces a viscous slurry that is very difficult to filter. The use of benzene and toluene gives results similar to those obtained with xylene. Several other types of solvents are also unsatisfactory for varying reasons.

The use of certain aliphatic solvents solves the filtration problem, but leads to another. Crude 2-ethylhexyl gallate is difficulty soluble in hot heptane, from which, on cooling, it crystallizes in readily filtrable form. However, the resulting crystals retain the colored impurities present in the crude product. Hexane gives similar results. Thus it is seen that there is a need for a solvent system which enables one to crystallize 2ethylhexyl gallate in the form of readily filtrable crystals which are essentially free of colored impurities.

SUMMARY OF THE INVENTION

It is an object of this invention to provide a simple method for reliably obtaining 2-ethylhexyl gallate in a form that is readily filtrable and is relatively free of colored impurities.

In accordance with the invention, it has now been found that pure 2-ethylhexyl gallate may be prepared by a process which includes treating crude 2-ethylhexyl gallate with a solvent system comprising a major proportion of a liquid aliphatic hydrocarbon solvent and an effective minor proportion of 2-ethylhexanol. 2-Ethylhexyl gallate crystallizes in readily filtrable form from a liquid aliphatic hydrocarbon solvent containing a minor proportion of 2-ethylhexanol. Furthermore, at ethylhexanol proportions above certain minimum levels, the colored impurities are largely retained in the solvent system leaving the ester product comparatively color-free.

DESCRIPTION OF PREFERRED EMBODIMENTS

As the aliphatic hydrocarbon components of the solvent systems used in the invention the preferred hydrocarbons are the paraffins having six through twelve carbon atoms, i.e, the hexanes, heptanes, octanes, nonanes, decanes, undecanes, and dodecanes. These include, not only the normal straight chain compounds, but also branched chain compounds, such as 2,2,4-trimethylpentane and iso-heptane, as well as synthetic mixtures, such as equal parts of n-hexane and n-heptane, and "naturally occurring" hydrocarbon mixtures such as gasoline, kerosene and ligroine (petroleum ether) obtained from petroleum refining operations. Particularly preferred are the six-carbon paraffins (hexanes), especially n-hexane.

The minimum proportion of 2-ethylhexanol in the solvent system will ordinarily be that required to produce a substantially color-free product. The maximum will, as a practical matter, often be determined by solubility/yield considerations. 2-Ethylhexyl gallate is more soluble in alcohols than in hydrocarbon solvents. Consequently, as the 2-ethylhexanol content of the solvent system increases the yield of product from the crystallization step tends to decrease.

The invention is further illustrated by the following examples.

In the work described below the hydrocarbon solvent was a commercial grade of n-hexane containing about 95–98% n-hexane, the remainder being primarily other saturated C-6 hydrocarbons.

EXAMPLE 1

Gallic acid is esterified with an excess of 2-ethylhexanol in toluene, using p-toluenesulfonic acid as an esterification catalyst. The cooled reaction mixture is washed with salt water to remove the catalyst and is then dried by azeotropic distillation. The mixture is filtered, and toluene and excess 2-ethylhexanol are stripped off under reduced pressure (50–60 mm Hg) until the pot temperature reaches 150° C. The 2-ethylhexyl gallate/ 2-ethylhexanol ratio in the residual oil is determined by NMR. The composition of the oil is then adjusted if necessary, to approximately 9g. 2-ethylhexyl gallate/g. 2-ethylhexanol, either by further vacuum stripping or by addition of 2-ethylhexanol, as the situation may require. Hexane (2.7 ml/g. 2-ethylhexyl gallate) is added, and the mixture is heated to 55°–60° C. With good agitation, the two-phase system is cooled to 20° C. and the crystalline 2-ethylhexyl gallate is collected. The cake is first washed with hexane/2-ethylhexanol (18/1), then with hexane. The colorless grainy product is dried under vacuum at about 30°–40° C. Yield, 80–85%, based on gallic acid charged to the reactor.

EXAMPLE 2

Crude 2-ethylhexyl gallate (12.9g., containing about 13% residual 2-ethylhexanol was heated with hexane (33.5 ml.) at 55° C. The mixture was stirred and cooled until its temperature dropped to 30° C. The product separated as colorless granular clumps of hexagonal crystals which are readily separated from the solvent by filtration. Yield of dry, essentially colorless product: 8.4g (74%).

EXAMPLES 3-6

The mother liquors from several runs carried out as described in Example 1 were combined, and the solvent was stripped off at reduced pressure and the ester/alcohol ratio adjusted as described in Example 1. Hexane was added to the dark oil and an additional crop of 2-ethylhexyl gallate was crystallized out and collected, as described in Example 1. The product, though grainy and easily filtered, retained some color.

Portions of the colored, crystalline 2-ethylhexyl gallate were recrystallized from hexane/2-ethylhexanol solvent systems of varying composition, with the results set forth in Table 1.

Table 1

Yield/Color Data on 2-Ethylhexyl Gallate
Recrystallized from Hexane/2-Ethylhexanol Solvent Systems

| Ex. No. | Ratio Hexane/ 2-Ethylhexyl Gallate (ml/g) | Ratio Hexane/ 2-Ethylhexanol (v/v) | Recovered 2-Ethylhexyl Gallate Yield (%) | Color |
|---|---|---|---|---|
| 3 | 6/1 | 99/1 | 99 | Sl. colored |
| 4 | 6/1 | 98/2 | 95 | Colorless |
| 5 | 6/1 | 96/4 | 81 | Colorless |
| 6 | 6/1 | 92.3/7.7 | 54 | Colorless |

Thus, it is seen that in this system somewhat more than 1% of 2-ethylhexanol is required for complete color removal and that yield considerations dictate a maximum of about 8% of the alcohol. The preferred range is about 2-5% of 2-ethylhexanol.

Since small amounts of 2-ethylhexanol are normally present in crude 2-ethylhexyl gallate, the former is the preferred additive to the hydrocarbon solvent for use in the purification of the latter. However, other aliphatic alcohols of about the same or somewhat higher molecular weights, generally in the 8-12 carbon range, may be substituted for or mixed with, the 2-ethylhexanol, with generally equivalent results.

Of course, the color removal/yield properties of other specific hydrocarbon/alcohol combinations will vary somewhat from those illustrated above, but one skilled in the art will be able to select preferred proportions of components in such other solvent systems with a minimum of experimentation.

In the embodiment wherein hexane is used as the hydrocarbon component of the solvent the preferred proportion of hexane to 2-ethylhexyl gallate is about 2.5 to about six ml. of hexane per gram of the gallate.

While the esterification of gallic acid with 2-ethylhexanol is the preferred method for preparing crude 2-ethylhexyl gallate, other known methods for preparing esters may be utilized, if desired. The crude products from such preparative methods are also susceptible to purification by treatment with hydrocarbon/2-ethylhexanol solvent systems as described herein.

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

We claim:

1. A method for preparing pure 2-ethylhexyl gallate which comprises treating crude 2-ethylhexyl gallate with a solvent system consisting essentially of a major proportion of a liquid aliphatic hydrocarbon solvent and a minor proportion of 2-ethylhexanol, the latter being present in a proportion of more than one percent and not more than about eight percent by volume, and separating pure 2-ethylhexyl gallate therefrom.

2. A method as defined by claim 1 wherein the liquid aliphatic hydrocarbon solvent is composed of paraffins of 6-12 carbons.

3. A method as defined by claim 2 wherein the hydrocarbon solvent is composed primarily of 6-carbon paraffins.

4. A method as defined by claim 3 wherein the hydrocarbon solvent is principally n-hexane.

5. A method as defined by claim 4 wherein the proportion of 2-ethylhexanol in the solvent system is in the range of about two to about five percent.

6. A method as defined by claim 4 wherein about 2.5 to about 6 ml. of n-hexane per gram of 2-ethylhexyl gallate is used.

7. In a method for preparing relatively pure 2-ethylhexyl gallate which comprises esterifying gallic acid with 2-ethylhexanol to form crude 2-ethylhexyl gallate containing 2-ethylhexanol, the improvement which comprises mixing the crude 2-ethylhexyl gallate with sufficient hexane to form a hexane/2-ethylhexanol solvent system in which the volume ratio of hexane to 2-ethylhexanol is not greater than about 99/1 and not less than about 92/8, and separating relatively pure 2-ethylhexyl gallate from the solvent system.

8. A method as defined by claim 7 wherein the volume ratio of hexane to 2-ethylhexanol is not greater than about 98/2 and not less than about 95/5.

9. A method as defined by claim 8 wherein about 2.5 to about 6 ml of hexane per gram of 2-ethylhexyl gallate is used.

10. A method for obtaining relatively pure 2-ethylhexyl gallate from crude 2-ethylhexyl gallate containing 2-ethylhexanol and colored substances as impurities, which method comprises forming a system containing 2-ethylhexyl gallate, 2-ethylhexanol and hexane in the approximate proportions of 9 grams 2-ethylhexyl gallate: 1 gram 2-ethylhexanol: 24 ml hexane, at an elevated temperature and separating relatively pure 2-ethylhexyl gallate therefrom.

11. A method as defined by claim 10 wherein the elevated temperature is about 55°-60° C.

12. A method as defined by claim 11 wherein the system is cooled to about 20° C. prior to the separation of the relatively pure 2-ethylhexyl gallate therefrom.

* * * * *